United States Patent
Rabin et al.

(10) Patent No.: US 9,724,445 B2
(45) Date of Patent: Aug. 8, 2017

(54) PERSONAL DEODORIZING PRODUCTS

(71) Applicant: LiveLVI LLC, San Rafael, CA (US)

(72) Inventors: Lisa S. Rabin, San Rafael, CA (US); Evan S. Edelist, San Rafael, CA (US)

(73) Assignee: LIVELVI LLC, San Rafael, CA (US)

( * ) Notice: Subject to any disclaimer, the term of this patent is extended or adjusted under 35 U.S.C. 154(b) by 0 days.

(21) Appl. No.: 14/956,286

(22) Filed: Dec. 1, 2015

(65) Prior Publication Data

US 2016/0151529 A1 Jun. 2, 2016

Related U.S. Application Data

(60) Provisional application No. 62/086,574, filed on Dec. 2, 2014.

(51) Int. Cl.
*A61L 9/05* (2006.01)
*A61L 9/013* (2006.01)
*A61L 9/014* (2006.01)

(52) U.S. Cl.
CPC .............. *A61L 9/05* (2013.01); *A61L 9/013* (2013.01); *A61L 9/014* (2013.01)

(58) Field of Classification Search
CPC .................................... A61L 9/00; A61L 9/05
USPC ............................................................ 512/5
See application file for complete search history.

(56) References Cited

U.S. PATENT DOCUMENTS

| | | | |
|---|---|---|---|
| 3,567,118 A * | 3/1971 | Shepherd | A43B 1/0045 15/104.93 |
| 3,762,875 A | 10/1973 | Burmeister | |
| 5,206,959 A | 5/1993 | Provenzano | |
| 6,251,431 B1 | 6/2001 | Van Rees | |
| 6,254,823 B1 * | 7/2001 | Rees | A61L 9/042 422/122 |
| 7,926,734 B2 * | 4/2011 | Dobler | A61L 9/12 239/52 |
| 8,966,674 B2 | 3/2015 | Lu | |
| 9,132,204 B2 | 9/2015 | McKay et al. | |
| 9,381,266 B2 | 7/2016 | Sherwood | |
| 2003/0091529 A1 | 5/2003 | Shah | |
| 2005/0053574 A1 | 3/2005 | Hill | |
| 2009/0032553 A1 | 2/2009 | Eddy | |
| 2010/0298195 A1 | 11/2010 | Franzolin et al. | |
| 2013/0248613 A1 | 9/2013 | Dobler | |

(Continued)

OTHER PUBLICATIONS

Pottymints, available at https://www.pottymints.com, retrieved on Sep. 22, 2016, 2 pages.

(Continued)

*Primary Examiner* — Lanee Reuther
(74) *Attorney, Agent, or Firm* — Dergosits & Noah LLP

(57) ABSTRACT

The invention relates to deodorizing products, and in particular, deodorizing products that find use in toileting. In some aspects, the deodorizing product is a solid substrate that disintegrates when exposed to water such as in a toilet bowl, where the solid substrate has been pre-infused with a scenting agent, for example, an essential oil or a microencapsulated essential oil. The composition can be placed directly into the toilet bowl water prior to toileting, thereby expediting the action of the scenting agent. After toileting, the scenting agent is substantially removed when the toilet is flushed. The invention can also be used as a deodorizing product without deployment in liquid water.

12 Claims, 5 Drawing Sheets

(56) References Cited

U.S. PATENT DOCUMENTS

2014/0018328 A1* 1/2014 Harrison ............ A61K 31/618
514/159
2014/0199257 A1 7/2014 Carter
2015/0108239 A1 4/2015 Bourne

OTHER PUBLICATIONS

Pottymints, available at https://www.pottymints.com/about, retrieved on Sep. 22, 2016, 2 pages.
Pottymints, available at https://www.pottymints.com/products-category/products/, retrieved on Sep. 22, 2016, 2 pages.
PCT International Search Report, Written Opinion of the International Searching Authority, Search History and Notification of Transmittal for PCT Application No. PCT/US2015/063276, with date of mailing Feb. 3, 2016; 12 pages total.
Washington Post Magazine, Lifestyle, "Gene tests the ultimate weapon against Poop Shame: Poo-Pourri" by Gene Weingarten, print edition Oct. 20, 2013; retrieved from < http://www.washingtonpost.com/lifestyle/magazine/gene-tests-the-ultimate-weapon-against-poop-shame-poo-pourri/2013/10/17/a3612500-27a6-11e3-b75d-5b7f66349852_story.html >.
Product brochure, "Aquasol® Water Soluble Paper and Tape," Aquasol Corporation < www.aquasolwelding.com >, retrieved from <http://www.aquasolwelding.com/wp-content/uploads/2014/08/Water-Soluble_Aquasol-Corporation-Brochure_HR_WSP-B2.0413.R2.pdf >, accessed on Feb. 24, 2016, on 4 pages.
Bakry et al., "Microencapsulation of Oils: A Comprehensive Review of Benefits, Techniques, and Applications," Article in Comprehensive Reviews in Food Science and Food Safety, published by Institute of Food Technologists®, Nov. 2015, DOI: 10.1111/1541-4337.12179.
Fairhurst and Loxley, "Micro- and Nanoencapsulation of Water- and Oil-soluble Actives for Cosmetic and Pharmaceutical Applications," Chapter 17: Cosmetic Delivery Systems, pp. 23-46, published by Particle Sciences, Inc. (Bethlehem, PA), published approximately 2008, retrieved from <http://www.particlesciences.com/docs/Micro_and_nano-encapsulation_of_Water_and_Oil_soluble_Actives_for_Cosmetic_and_Pharmaceutical_Applications.pdf>.
The Dallas Morning News, Biz Beat Blog, "Dallas-based Poo-Pourri sues after sniffing out V.I.Poo similarities" by Todd Davis, published Mar. 9, 2016; retrieved from, < http://bizbeatblog.dallasnews.com/2016/03/dallas-based-poo-pourri-sues-after-sniffing-out >, accessed Jun. 30, 2016.
Poo Pouni Products Listing, All Products, retrieved from <http://www.poopourri.com/collections/all-products>, accessed on Jul. 5, 2016; earliest date of availability unknown; on 80 pages.
Just a Drop(R) Website Homepage, retrieved from < www.justadrop.com >, accessed on Jun. 30, 2016; on 9 pages; earliest date of availability unknown.
Just a Drop(R) Product Descriptions, retrieved from < www.justadrop.com/product-category/justadroporiginal/>, accessed on Jun. 30, 2016; on 3 pages; earliest date of availability unknown.
Just a Drop(R) Product Description, Poopee Chic(TM) Preemptive Potty Spray Oh Crap(TM), retrieved from < www.justadrop.comishop/poopeechic/oh-crap/>, accessed on Jun. 30, 2016; on 2 pages; earliest date of availability unknown.
Prelam(TM) Enterprises Ltd., website brand descriptions, retrieved from <prelam.com/our-brands/>, accessed on Jul. 5, 2016; on one page; earliest date of availability unknown.
Notification Concerning Transmittal of International Preliminary Report on Patentability for PCT/US2015/063276, dated Jun. 15, 2017, 7 pages.

* cited by examiner

PERSONAL DEODORIZING PRODUCTS

CROSS-REFERENCE TO RELATED APPLICATIONS

This application claims priority to and benefit of U.S. Provisional Application Ser. No. 62/086,574, filed on Dec. 2, 2014, which is herein incorporated by reference in its entirety.

FIELD OF THE INVENTION

The invention relates generally to air deodorizers and air fresheners, especially with regard to toileting deodorizers.

BACKGROUND OF THE INVENTION

Users of shared restrooms in public settings such as office buildings, dormitories, hotels, airports, and residences such as homes and apartments, have social discomfort in offending others with embarrassing odors that arise while using a toilet or with odors that may persist after using the toilet. This concern of embarrassment can be particularly significant in individuals suffering from various gastrointestinal disorders such as ulcerative colitis, Crohn's disease, Irritable Bowel Syndrome, celiac disease, lactose intolerance, gastrointestinal infections and other disorders. Concern for concealment of bathroom odors is also elevated after eating certain types of foods which result in particularly pungent stool or urine, or result in elevated gaseousness, such as foods rich in sulfurous compounds, red meat and many types of vegetables.

There exist a variety of currently marketed deodorizing products intended to reduce unpleasant toilet odors. However, these existing products all suffer from various shortcomings.

Aerosol sprays are a commonly used deodorizing product. This dispensing system uses pressurized gas to propel liquid out of a metal can (termed a propellant gas), thereby creating a fine mist of atomized liquid particles. The most commonly used propellants are combinations of hydrocarbons, primarily butane, propane and isobutane—all of which are highly flammable. There are several health concerns surrounding the use of aerosols, most significantly the inhalation of chemical spray components which can be respiratory irritants. Aerosol sprays, as well as other types of deodorizing products, can also be accompanied by undesirable chemical odors, for example, as caused by a liquid carrier or an aerosol propellant.

Pump spray products use a manual hand action to create a mist or spray of liquid, but without the use of propellants. They often incorporate an alcohol as a carrier for the aromatic agent in the formulation. These liquid products also generate potentially irritating airborne particles. Furthermore, the non-directional application of aerosol or spray-pump products can harm finished surfaces and may leak, spill or drip.

Liquid products that are directly applied into the toilet bowl, for example, by a dropper mechanism, also have drawbacks. These types of products are prone to over-application, and can impart an undesirable overpowering fragrance to the environment that is difficult to modulate. Liquid drop products also carry a high risk of spillage and dripping.

Multiuse containers for the application of deodorizing agents, such as spray cans, hand pumps and dropper-style applicators, all carry an additional risk in that they are inherently unsanitary. Because these types of containers are handled prior to and after toileting affairs, most frequently by multiple individuals, they can act as vehicles for disseminating microbial and viral pathogens, and other types of pathogenic organisms.

Devices that continually emit a fragrance outside of the toilet bowl and/or in the toilet room are also known. Plug-in devices that continually emit fragrance are limited in their use in that they are not portable and require an AC power source. Similarly, battery powered devices suffer from the same limitation in that they require a DC power source. Any device that continually emits a masking scent, including plug-in devices, battery-operated devices, and other devices that do not require a power source, frequently have the drawback that the continuous scent emitted from the device itself become overpowering and noxious when the user no longer needs a cover-up fragrance.

Deodorizing devices that incorporate a water reservoir in conjunction with scented ingredients are potentially reservoirs for unwanted microbial growth, in particular, mold. This includes homemade deodorizing sprays.

The persistence of strongly scented deodorizing agents such as any of those described above can also be equally embarrassing in that they are indicative of the toilet user's activities.

What is needed in the art are deodorizing products that do not contain propellant gasses, are not overpowering in scent, do not spray or drip, do not contain irritants or chemical odors, are sanitary, and are portable and discrete. The present invention, in its many embodiments, provides compositions and methods that overcome these challenges in the industry, and provide many benefits over the state of the art previously unrealized in other types of personal deodorizing products.

The presently described invention differs from existing products in many unique and beneficial ways, and one of skill in the art will appreciate the variety of benefits that flow from the invention. For example, the invention is single-use, i.e., sanitary, and not shared between multiple users; it is easily portable and physically discrete, and can be concealed in a pocket, wallet or handbag; is leak-proof, spill-proof and will not drip; and the product emits a subtle and temporary scent, effectively reducing, eliminating or masking unpleasant toilet odors. The invention product can be a natural and/or non-toxic deodorizing product. The invention has a variety of deodorizing applications. Still further benefits flow from the invention described herein, as will be apparent upon reading the present disclosure.

SUMMARY OF THE INVENTION

The present disclosure provides compositions and methods for deodorizing finding particular use in masking unpleasant toilet odors. In some aspects, the deodorizing product is, in part, a solid substrate that disintegrates when exposed to water, such as in a toilet bowl. The solid substrate has been pre-infused with an oil scenting agent, for example, an essential oil. The composition can be placed directly into the toilet bowl water prior to toileting, thereby expediting the action of the scenting agent. After toileting, the scenting agent is removed when the toilet is flushed.

The solid substrates used with the invention are not limited to the particular embodiments recited herein. In some embodiments, the solid substrate is a cellulose-containing paper product that rapidly disintegrates upon contact with water. Alternatively, the use of rapidly-disintegrating synthetic paper-like products are also contemplated. Other types of suitable solid substrates are also contemplated, where the solid substrate has the essential features of serving as a substrate for adsorption of a scented oil and is capable of disintegrating upon contact with water.

The amount of a scented oil that is applied to the aqueous-disintegratable solid substrate will be generally sufficient to abate unpleasant odors when placed near the source of the unpleasant odors such as toileting odors. In some embodiments, the disintegratable solid substrate infused with a scented oil is placed in water such as the water in a toilet bowl.

Any type of scented oil finds use with the invention. For example, essential oils, absolute oils and synthetic fragrance oils all find use with the invention, as well as any blends of any types of scented oils. Carrier oils can also be used in conjunction with the invention. In other embodiments, the deodorizing products of the invention are manufactured using microencapsulated scented oils that are applied to the solid substrate.

In some embodiments, the scent-infused solid substrate is individually packaged. The package can be advantageously impervious to water, and blocks the diffusion of scent-inducing molecules so that the scent of the product does not leach out of the packaging into the environment until the package is opened. Packaging can also be opaque to minimize the risk of photodegradation.

In some embodiments, the invention provides methods for making the deodorizing product described herein. The methods essentially include a first step of providing (i) an aqueous-disintegratable solid substrate, most commonly a rapidly disintegrating paper product, and (ii) a non-aqueous scented liquid, most commonly a scented oil which can be an essential oil, an absolute oil, a fragrance oil, a plurality such oils, or any type of combination or blend of any such oils. In the second step, the non-aqueous scented liquid is infused into the solid substrate by applying the oil to the substrate, thereby producing the deodorizing product. Optionally, the method can further include sealing the scent-infused solid substrate into suitable packaging, for example, packaging that uses materials that are substantially impervious to water.

The deodorizing compositions of the invention find a variety of uses. Uses include, for example but not limited to, reducing toileting odors, or any other location that contains unpleasant odors. In some embodiments, use of the product entails placing the product in water, such as in the water in a toilet bowl. In other embodiments, deployment of the product does not entail placing the product in water.

The use of bulk dispensers to house and dispense the personal deodorizing products of the invention in locations such as public restrooms is contemplated. Designs for bulk dispensers are provided and are a feature of the invention.

DETAILED DESCRIPTION OF THE INVENTION

The invention provides compositions and methods related to the manufacture and use of personal deodorizing products, for example, products that can be used to mask unpleasant toileting odors. Generally, the product is a solid substrate that can rapidly disintegrate in water, for example, using specially designed paper products, where that solid substrate has been pre-infused with at least one pleasantly scented aqueous-immiscible (e.g., hydrophobic) liquid, for example, a scented oil such as an essential oil.

The compositions of the invention are produced by applying any suitable scented oil (a hydrophobic liquid) to the aqueous-disintegratable solid substrate. The application of the scented oil can be by any means, for example, by soaking the substrate in the oil, or by dispensing a fixed regulated volume of the oil to the solid substrate. The amount of oil applied to the substrate will be generally sufficient to mask the unwanted odors, which can be determined empirically. The intensity of the scent that emanates from the product can be regulated by varying the concentration of the scented oil that is applied to the solid substrate, or by regulating the volume of the scented oil that is applied to the substrate.

As used herein, the terms "scent," "scented," "fragrance," "fragranced" or "perfumed" refer to pleasing or agreeable olfactory responses, e.g., a pleasant smell or a smell that induces positive emotions or recalls memories of positive personal experiences. As used herein, the terms "odor" or "odorous" refer generally to unpleasant and undesired olfactory responses, e.g., an unpleasant smell, such as toileting odors.

Figure 2:
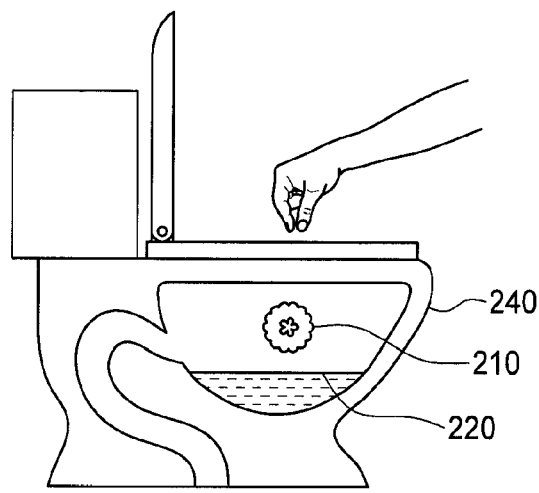
FIG. 2 provides an illustration depicting the use of a deodorizing sheet of the invention.

In one embodiment, a product of the invention comprises a water-disintegratable paper that has been infused with a scented oil, and intended for personal use to mask toilet odors. Use of such a product is illustrated in FIG. 2. Preferably immediately prior to using the toilet, the user simply drops the product 210 into the toilet bowl 240 so that it will rest and float on the surface of the water 220.

Figure 3:
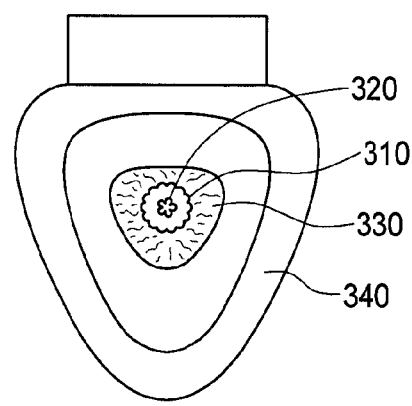
FIG. 3 provides a top-view illustration depicting the deployment of a deodorizing sheet of the invention in the water of a toilet bowl.

FIG. 3 shows the product depicted in FIG. 2 that is deployed in a toilet. The deodorizing product 320 comes to rest on the surface of the water 330. The paper substrate rapidly loses structural integrity and disintegrates upon exposure to the toilet bowl water, resulting in the dispersal of the scented oil, typically forming a thin barrier film 310 on the surface of the water 330 in the toilet bowl 340. The barrier film of oil in the toilet water may or may not be visible to the user.

After dispersal of the scented oil layer in the toilet bowl water as shown in FIG. 3, molecules of that surface film aerosolize and generate a pleasing scent, thereby masking or reducing the unpleasant toileting odors from stool, pungent urine or intestinal gasses. In addition, the oil film on the surface of the water creates a mechanical barrier to the release of unpleasant odors of stool or pungent urine from the water. This barrier also traps unpleasant odors from the stool that passes through the oil layer and falls into the water. The products of the invention thereby mask or reduce unpleasant toileting odors. In alternative embodiments, the deodorizing products of the invention need not be placed in water to effectively mask toileting odors, where simply opening a sealed package containing a product of the invention is sufficient to mask toileting odors or any other odors.

The present disclosure provides discussion of mechanistic theories explaining how the invention acts to reduce or mask toileting odors. However, it is not intended that the invention be limited in any regard to the molecular mechanism of action, and knowledge of such mechanisms is not required to make or used the invention. It is not intended that the term "deodorizing" as used herein be limited in any way with regard to the mechanism by which the deodorizing is occurring.

After the user is done toileting, they simply flush the toilet. The oil that remains in the toilet bowl after toileting is substantially removed when the toilet is flushed, and thus, does not continue to produce an overwhelming persistent fragrance in the surrounding environment for an extended time. In this way, the product does not continue to generate excessively strong or overpowering scents that might in themselves oversaturate the air in the room and be irritating or embarrassing. Debris from the disintegration of the solid substrate, e.g., the material produced from the disintegration of the paper, is safely biodegradable and is also removed when the toilet is flushed.

In other embodiments, a deodorizing product of the invention can be deployed to mask toileting odors without placing the product in the toilet bowl water. In that scenario, the scent emanating from the dry scented disk is sufficient to mask the toileting odors. After toileting, the user can either leave the dry product in place in the toileting room for continuing deodorizing activity, or the user can flush the product down the toilet to halt the on-going deodorizing effects of the scented substrate.

Qualitative empirical testing was used to test the efficacy of the invention to reduce unpleasant toilet odors. The testing was conducted using an aqueous-disintegratable paper substrate, namely, AQUASOL® water soluble paper (Aquasol Corporation, North Tonawanda, N.Y.) product number ASW-35/S, which has a thickness of 0.0035 inches. Variously shaped paper outlines were used, both with and without cut-outs or perforated sections. Disintegratable papers having a range of surface areas were also tested, for example, disk shapes having various diameters. A variety of scented oils were applied (adsorbed) onto the disintegratable paper. These test products were given to toilet users, who were then polled about the effectiveness of the product to reduce or mask toilet odors. After toileting matters were completed, the test users found a significant reduction or elimination of unpleasant toilet odors emitted into the environment with all of the products tested.

In some embodiments, a faint scent from the scented oil in the product advantageously remains in the local toilet environment for a short time after flushing, for example, for a matter of seconds up to about one minute, or for a period of time from about one to about five minutes, depending on ventilation and size of the room where the toilet is located. A faint lingering scent is preferred over a lingering strong, overpowering scent. It is desirable that the scent from the product not linger in the toilet environment for a particularly long period of time.

Qualitative testing to determine the lingering effects of deploying the deodorizing sheets of the invention was conducted. The testing used low-flow style toilets (1.6 gallons and 1.28 gallons per flush), single and dual-flush model toilets, and older high volume toilets (3.5 gallons per flush). The testing used disintegrating paper deodorizing sheets ranging in size from 1.5 inch diameter disks to 4.0 inch diameter disks. It was observed using each of these toilet styles, and using all tested paper sizes, that the scent of the oil was significantly reduced after flushing.

In the case of particularly strong persistent toilet odors, a supplemental deodorizing sheet can be dropped on the surface of the water after flushing. Alternatively, or in addition, a user can also leave an opened deodorizer sheet package in the room to mask persistent toilet odors.

The product has a secondary benefit that makes it suitable for a variety of uses. After being removed from any airtight packaging, it produces a light scent that is released into the air even without being placed in water. In this manner, the product can also be used in a variety of other locations to mask unwanted odors.

The compositions and methods of the invention have clear advantages over the state of the art. Products of the invention are highly portable, and comprise a small sheet of paper, for example but not limited to, a disk shape not more than about two inches in diameter. This small piece of disintegratable paper infused with a scented oil can be packaged in air-tight and water-tight packaging that is also advantageously small and discrete. Products of the invention are hygienic, in that the products are for single use, and are handled by only one person (i.e., not shared), thereby minimizing or eliminating the risk of passage of microbial or viral agents, or other pathogenic organisms between users. Products of the invention do not contain any flowing liquids, therefore, do not carry a risk of spilling, leaking or dripping. Products of the invention do not require any aerosol propellant gasses. Products of the invention have a further advantage in that their scenting effect is relatively short lived, for example, only have a scenting activity between the time that the user opens the product packaging and the time that the user flushes the toilet. This window of scent activity is advantageous in avoiding embarrassment from the overpowering and irritating scents that can linger in the toilet when excessively strong deodorizing products are used.

I. Disintegrating Substrates

The deodorizing product of the invention comprises a solid substrate that disintegrates when placed in contact with liquid water. A variety of suitable substrates is known, and can find use with the invention. The structure and specification of the water-disintegratable substrate is not particularly limited. The disintegrating substrate can be a product derived from a natural source, for example, plant material, including naturally-occurring celluloses. In other aspects, the solid substrate can be a suitable synthetic material, or can comprise artificially manufactured materials. The solid substrate can comprise any combination of natural and synthetic materials.

As used herein, the expressions "aqueous-disintegratable" or "water-disintegratable" or "water-disintegrating" or similar and equivalent expressions are used to describe materials that rapidly disintegrate or dissociate when exposed to liquid water. The disintegration that occurs is rapid, in contrast to "decomposing" which refers to a biological decay process that occurs over a longer time period.

As used herein, the terms "dissolve" or "dissolving" refer to one compound passing completely into a solubilized state in a given solvent. For example, when a compound "dissolves" in water, there is no solid or particulate or colloidal aspect left to that compound. The compound is said to be entirely in solution. For example, salt (sodium chloride) readily dissolves in water, i.e., salt is highly soluble in water.

In some embodiments, the solid substrate is most commonly a specially manufactured paper that disintegrates when placed in contact with water. The disintegration of the paper in the water is rapid and thorough, where the paper disintegrates in a matter of seconds, typically less than one minute. The particulate remnants of the paper that remain in the toilet bowl water are of a size and nature that can be safely flushed down the toilet along with the contents of the toilet bowl after toileting.

A paper-style disintegrating substrate can be a true paper traditionally containing cellulose derived from wood pulp or other fibrous plant material, or it can be a synthetic product such as a rapidly disintegrating synthetic paper, or be a combination of plant material and synthetic material. Regardless of the actual structure of the product, that substrate disintegrates when placed in unagitated water in a reasonably short period of time, for example, in a time interval that does not exceed about one minute, or about 45 seconds, or 30 seconds, or 20 seconds, or 10 seconds, or 5 seconds, or 3 seconds. Deodorizing sheets of the invention that use disintegrating paper substrate disintegrate when placed in unagitated water in about five seconds. For comparison, a one inch diameter disk of a single-ply toilet paper disintegrates with active agitation in about one minute and 50 seconds.

The deodorizing sheets that use a paper-type substrate can be of any size. In one aspect, the size of the deodorizing sheet is measured as a two-dimensional area, e.g., measured in square inches ($in^2$) or square centimeters ($cm^2$). The particular size that is used is not particularly limited, except that a small deodorizing product is generally preferred so that the product remains discrete and inconspicuous. A range of different sized paper-style deodorizing sheets have been manufactured and successfully tested. These products were generally disk-shaped, and were produced with and without outline ornamentation, for example, a scalloped border. Products were also manufactured with or without interior ornamentation, e.g., cut-out holes or perforations. The paper disks thus manufactured ranged in diameter sizes as small as 1.5 inches and as large as seven inches.

Figure 1:
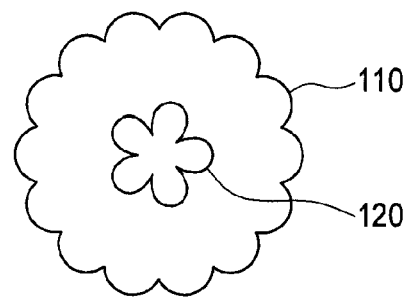
FIG. 1 provides an illustrated example of a single decorative deodorizing product of the invention.

FIG. 1 provides one illustrative, non-limiting example of a paper-style deodorizing product measuring 1.875 inches in diameter, and having a scalloped border 110 and a daisy-shaped interior cut-out portion 120.

Generally, a large deodorizing sheet will provide more deodorizing strength compared to a smaller deodorizing sheet having a smaller two-dimensional area, e.g., fewer square inches. Strength of the scent in a single product can also be regulated by the volume or concentration of the scented oil that is applied (e.g., adsorbed or infused) into the paper substrate.

In some embodiments, it is desirable to fold the scented paper product prior to individual packaging so that the resulting packaged product remains minimal in size so that it remains discreet and inconspicuous.

In some embodiments, when a paper or paper-style substrate is used, the construction of the sheets can be a single-ply product. In other embodiments, the deodorizing sheets can be multi-ply, such as double-ply or triple-ply. Use of multi-ply sheets is advantageous when it is desirable to load larger volumes of a scented oil onto the solid substrate, compared to the volumes of the scented oil that can be loaded onto a single-ply product. When a single-ply or multi-ply product is used, the disintegration time of the sheet when placed in the water of the toilet bowl can be optimized (i.e., shortened) by designing the sheet to have holes or any type of perforations on or through the sheet or any kind of stamping that hastens the wetting and disintegration of the single-ply or multi-ply sheet.

The deodorizing sheets that are infused with at least one scented oil can be any desired design, shape, size, color, decorative pattern, or the like. In some embodiments, the sheets can be circular, or alternatively, square, or any desired patterned outline, for example, resembling a flower, a sun, or any other aesthetically pleasing pattern. In some embodiments, the deodorizing sheets are colored and/or can contain alphanumeric printing or any printed design of any type or color.

In various embodiments, the deodorizing sheets of the invention are unadorned circles of paper substrate. In other embodiments, the deodorizing sheets are substantially circular disks that have a decorative outline. In one aspect, such an outline can mimic or be reminiscent of a traditional doily pattern, as commonly used in embroidered lace-work decorative food placemats or printed patterns on paper napkins. See, for example, the deodorizing sheet of FIG. 1. All figures herein are intended to illustrate possible embodiments of the invention, and are not intended to limit the invention in any aspect.

The optional patterns used on the deodorizing sheets of the invention can be produced using any suitable method, for example, by die-cutting (also known as a dye punch) or laser cutting. For example, the product can be produced using single pattern die punches, as illustrated in products such as EK TOOLS™ scalloped disk punch, EK TOOLS™ daisy punch, MARTHA STEWART CRAFTS® daisy medallion punch, MARTHA STEWART CRAFTS® large double punch embroidery or WE R MEMORY KEEPERS™ 4 inch lattice doily die. Any combination of any number of die punches or embossing equipment can be used to manufacture the products of the invention. The equipment cited above is intended for home craft projects, but the decorative patterning and mechanical principles of which can be easily scaled up for larger volume manufacturing.

The decorative patterns used in the products can optionally contain any additional holes, piercings, perforations (large or small) or any kind of stamped or embossed patterning. As used herein, a hole refers to an empty space, hollow place or cavity that generally has a measurable area devoid of material. As used herein, the term "perforation" refers to a very small hole, puncture or piercing, commonly in a pattern of more than one perforation that collectively form a decorative element. Interior holes, perforations, piercings, embossing, or the like can be produced by any suitable process known in the art, for example, by any kind of mechanical stamping, pressing, piercing, rolling, laser cutting, or the like.

In some embodiments, the deodorizing product of the invention comprises optional ornamental designs that include irregular non-linear outlines, and/or internal holes, piercings, pressure stamping, embossing, and/or perforations in any pattern, areas, rows or any other arrangement. In those embodiments, the ornamental design can serve a functional purpose as well as a decorative purpose. Holes, perforations and any other surface irregularity generate increased surface area that expedites the wetting of the surface of the paper material and thereby accelerating the disintegration of the paper sheet in water, for example, the water in a toilet bowl. See, for example, the deodorizing sheet product shown in FIG. 1 containing a center perforated region 120 and a scalloped border outline 110.

Perforations, holes (excised regions) or any kind of piercings can be incorporated into the design to any extent, for example, can encompass between 10-75% of the paper base substrate depending on the pattern used. In some embodiments, a maximum efficiency in the rate of paper disintegration, oil dispersion and scent emission is achieved with approximately 35% perforation of the paper base substrate. Excessive perforations or excised areas, for example, in excess of 75% of the area of the product, may result in products that lose structural integrity or are unable to hold sufficient quantities of scented oil.

Thus, such decorative patterning has both an aesthetic purpose that is attractive and evocative of cleanliness, and a practical purpose in that the user need not wait an extended time for the product to take effect after dropping the scented sheet into the toilet bowl. However, the invention is not limited in any regard with respect to the outline of the product or any decorative elements that are incorporated into a deodorizing sheet of the invention.

Deodorizing sheets of the invention with and without decorative ornamentation were tested for the time required for the paper to disintegrate, and for their ability to mask offensive toilet odors. It was observed that the decorative sheets disintegrated in about 5 seconds, compared to about 10 seconds for products that do not contain the decorative elements. No difference was observed between the products for their ability to mask offensive toilet odors.

In one example, the deodorizing product is constructed from AQUASOL® water soluble paper (Aquasol Corporation, North Tonawanda, N.Y.). For example, AQUASOL® water soluble paper product number ASW-35/S is used, which has a thickness of 0.0035 inches. This paper is constructed of sodium carboxyl methyl cellulose and wooden pulp. It was found that water-soluble papers having thickness of between 0.0025 inches and 0.005 inches was suitable for use with the invention. It was observed that thinner water-soluble papers outside this range do not adsorb sufficient quantities of scented oil and are difficult to handle, for example, are fragile. Conversely, papers that are thicker than this recited range generally do not disintegrate quickly enough to work conveniently as a toilet deodorizer when placed in water. However, deodorizing products that use a disintegratable paper thicker than 0.005 inches still find use with the invention, for example, in applications other than those that require exposure to water.

In other embodiments, aqueous-disintegratable solid substrates other than disintegrating papers are contemplated. These alternative products all have the features of disintegrating upon contact with water and can serve as a substrate for adsorption of a scented oil. It is not intended that the invention be limited to disintegratable papers. For example, it is contemplated that the solid substrate can be an aqueous-soluble carbohydrate disk, such as a thin cohesive sugar disk, a thin cohesive disk of a salt, or any flowing water-soluble granular power of any type, for example, a granular salt or a granular carbohydrate such as a sugar. Other types of suitable solid substrates are also contemplated, including rice paper and gelatin sheets.

II. Scented Oils

The scented liquids that are pre-infused into the water-disintegratable sheets are not particularly limited. In some embodiments, the scented liquids are scented oils, for example, essential oils or fragrance oils that have a pleasing scent. One of skill in the art will be familiar with a wide variety of scented oils, including essential oils, absolute oils, fragrance oils and various formulations for combinations of scented oils, any of which can find use with the invention.

As used herein, the term "aqueous" refers to water, or solvents or mediums that are water-based solutions. As used herein, the term "non-aqueous" refers to liquids or solvents that do not incorporate water as the primary solvation media. Non-aqueous liquids are most frequently hydrophobic, e.g., they do not dissolve in water. Non-aqueous liquids, e.g., oils, are most frequently "immiscible" in water, referring to their inability to mix (inability to form true homogenous solutions). Attempts to mix oils with water will generate an emulsion, where the oil phase and aqueous phase remain separate.

As used herein, the term "oil" refers generally to neutral, non-polar substances that are liquid and viscous at ambient temperatures. They are hydrophobic (immiscible with water), and will form a distinct layer that rises to the surface when mixed with water or any aqueous liquid. The broad term "oil" includes classes of chemical compounds that may be otherwise unrelated in structure, properties and uses.

As used herein, the term "scented oil," "aromatic oil" or similar or equivalent terms or expressions refer to any oil that contains compounds that impart a scent to the oil. As used herein, the term "scented oil" includes the narrower categories of "essential oils," "absolute oils" and "fragrance oils" (fragrance oils alternatively known as "perfume oils"). Scented oils can refer to a single oil, or can refer to any combination of any type of oils, including mixtures of essential oils, absolute oils and/or fragrance oils. Scented oils can be formulated in a carrier oil. Any scented oil need not be a "pure" oil in that the oil is not a pure molecular species. Any aromatic oil, including scented oils, typically contain many different molecular species.

As used herein, the term "essential oil" or similar or equivalent terms or expressions refer to the concentrated oils obtained from plants that contain volatile naturally-occurring aromatic compounds characteristic of that plant. Essential oils are most frequently obtained by using a steam distillation process, although other isolation technologies can be used. Essential oils are alternatively known as volatile oils, or simply as the oil of the plant from which they were extracted, for example, lavender oil. An oil is "essential" in the sense that it contains the "essence" of the plant's characteristic fragrance. Although essential oils are isolated from plant material, the oils thus obtained are not themselves pure molecular species. Essential oils are complex mixtures of many compounds, sometimes up to as many as 500 different molecular species. A purified essential oil that has not yet been diluted, processed or manipulated with solvents or other additives is termed "neat."

As used herein, the term "absolute oil," also known as "absolutes" or an "essence oil" or similar or equivalent terms or expressions refer to the plant-derived, concentrated oils that contain the naturally-occurring aromatic compounds characteristic of that plant. Absolute oils are similar to essential oils in many respects, with the exception that absolute oils are produced by a process of solvent extraction, in contrast to essential oils that use a process of steam extraction. Traditionally, absolute oils are also produced through the process of enfleurage. There are subtle differences between essential oil products and absolute oil products. Absolutes are often more concentrated in the aromatic compounds compared to essential oils. The efficiency and low temperatures of the solvent extraction process used to produce absolutes helps prevent damage to fragrant compounds that can occur with harsher steam distillation processes that are used to produce essential oils. Absolute oils often preserve the naturally-occurring plant color in addition to the characteristic scent of the plant. Some scented oils are more commonly produced as an absolute oil, not an essential oil, for example, jasmine oil.

Some aromatic plant oils can be produced as either an essential oil or an absolute oil. For example, rose oil can be produced as an essential oil or a true absolute oil. Similarly, orange blossom absolute (from solvent extraction) and neroli essential oil (from steam distillation) are made using flowers of the same tree. In addition, other processes are available for the production of scented oils that are not strictly steam distillation processes or solvent extraction processes. Other methods for the production of scented oils include dry distillation, vacuum distillation, superheated destructive distillation, expression (also known as cold pressing, e.g., to produce citrus peel scented oils), production of concretes, pressurized carbon dioxide extraction, and collection of natural exudates and resins (or resinoids).

As used herein, the term "fragrance oil" (also known as "perfume oil") or equivalent terms or expressions refer to artificially manufactured aromatic oils. Fragrance oils can be formulated to mimic the scent of a naturally occurring product (for example, lavender fragrance oil is a synthetic oil that mimics the aroma of the naturally occurring oil derived from lavender plants). Alternatively, fragrance oils can emit non-naturally occurring scents that are pleasant and intended to invoke pleasing images or emotions. A wide variety of fragrance oils are known and available to one of skill in the industry.

There exists inconsistency in nomenclature and commercial labeling of scented oils. The term "essential oil" is often loosely applied to any scented oil regardless of source of the oil, method of isolation or method of synthesis. Regardless, any scented oil finds use with the invention, and it is not intended that the invention be limited to any type of scented oil or limited to a scented oil produced by any particular process. Furthermore, any type of naturally-occurring scented oil finding use with the invention can be optionally certified organic.

As used herein, the expression "carrier oil" refers to a base oil that is used to dilute some other oil, for example, an aromatic essential oil. For example, when used to dilute an essential oil, the carrier oil and essential oil mixture is made in order to better control the concentration and properties of the essential oil. Carrier oils do not typically contain their own concentrated aromas. Carrier oils also are generally less volatile and more stable than essential oils, as a result, are not prone to evaporation as quickly as essential oils. Carrier oils are often carbon-based, naturally occurring (organic) oils, such as vegetable oils, but can also be inorganic oils, such as mineral oil.

Carrier oils finding use with the present invention can be any type of suitable carrier oil, including oils extracted from natural sources, or synthetic carrier oils, or can be organic or inorganic. Suitable carrier oils are well known to one of skill in the art, and can be selected and obtained from a variety of commercial sources. Selection of a suitable carrier oil, or blends of carrier oils, will take into account a range of oil properties relevant to the intended use of the product. For example, selection of a suitable carrier oil that is optimized for manufacture of the present invention will take into account properties of the carrier oil such as viscosity, propensity for adsorption onto the solid substrate, any inherent aroma of the carrier oil, as well as consumer appeal.

In some embodiments, the oil that is infused into the paper substrate to produce the deodorizing sheets is a mixture of a scented oil, for example, an essential oil, and a carrier oil, where the carrier oil facilitates application of the oil component to the disintegrable paper substrate. The use of a carrier oil in conjunction with an essential oil also facilitates careful regulation of the dosage of strongly scented essential oils that that are applied to the paper substrate. Blends of more than one scented oil, including blends of essential oils and fragrance oils, with or without a carrier oil vehicle, also finds use with the invention.

Generally, in construction of the invention, the solid substrate, for example, the water-disintegrating paper, is infused with the scented oil. The scented oil can be from a single source, or be in any type of blend of a plurality of oils. The oil, for example, an essential oil, that is applied to the solid substrate, e.g., the paper, can be neat (undiluted), or alternatively, can be diluted with a suitable carrier oil, such as a generic mineral oil, in any suitable ratio, for example, between about 5% and 100% volume of the scented oil, with the remainder of volume provided by the carrier oil (if necessary). Some formulations require application of neat, 100% (undiluted) scented oil (e.g., a neat essential oil) without any carrier oil. When blends of scented oils are used, the blends are typically prepared using non-reactive vessels.

Non-limiting examples of scented oils and oil blends are listed below.

| Scent | Formulation (Volume Ratios)/Source |
| --- | --- |
| Lavender-Peppermint Blend | 65% lavender essential oil, and 35% peppermint essential oil. |
| Lavender | NOW ® 100% pure lavender essential oil |
| Peppermint | PLANT THERAPY ® 100% pure peppermint essential oil |
| Wintergreen | PLANT THERAPY ® 100% pure wintergreen oil |
| Apricot-Freesia Blend | BRAMBLE BERRY ® apricot freesia fragrance oil |
| Grapefruit | NOW ® 100% pure grapefruit essential oil |
| Cinnamon Leaf | AURA CACIA ® cinnamon leaf 100% pure essential oil |
| Lime | BRAMBLE BERRY ® lime fragrance oil |
| Mint Blend | 50% PLANT THERAPY ® 100% pure peppermint essential oil, and 50% PLANT THERAPY ® 100% pure wintergreen essential oil |
| Lavender-Mint Blend | 50% PLANT THERAPY ® peppermint oil, and 50% NOW ® lavender oil |
| Lavender-Lime Blend | 50% BRAMBLE BERRY ® lime fragrance oil, and 50% NOW ® lavender oil |

-continued

| Scent | Formulation (Volume Ratios)/Source |
|---|---|
| Citrus Fresh Blend | 50% NOW grapefruit oil, 30% BRAMBLE BERRY® lime oil, and 20% NOW® lavender oil |
| Refresh Blend | 40% NOW® grapefruit oil, 40% NOW® lavender oil, and 20% PLANT THERAPY® peppermint oil |
| Cinnamint Blend | 40% AURA CACIA® cinnamon leaf oil, 40% PLANT THERAPY® peppermint oil, and 20% PLANT THERAPY® wintergreen oil |
| Spring Blend | 30% BRAMBLE BERRY® apricot-freesia oil, 30% BRAMBLE BERRY® lime oil, and 40% NOW® lavender oil |

Solid substrate, e.g., the water-disintegratable paper, is infused with any suitable scented oil or oil blends. As used herein, the term "infused" means that the oil has been applied to and adsorbed by the solid substrate. The method for application of the scented oil to the substrate is not limited in any aspect. That is to say, the means for infusing the solid substrate with the scented oil is not limited. The infusion can be saturating or non-saturating. The infusion can be accomplished by immersion of the paper substrate into a scented oil, soaking, dipping the paper substrate in the scented oil, spraying the scented oil onto the paper, brushing the oil onto the paper, spotted onto the paper, or simply by placing drops or some premeasured volume of the scented oil onto the paper substrate.

The deodorizing products can be manufactured in varying strengths. The strength of the product can be modulated either by varying the volume of scented oil formulation that is applied to the paper (fixed concentration of the applied scented oil), or can be controlled by adjusting the concentration of the aromatic component that is in the applied oil (fixed volume of application).

In some embodiments, the solid substrate such as paper can contain infused components in addition to a scented oil. For example, deodorizing products further infused with antimicrobial compounds, or more broadly disinfecting agents, also find use with the invention. Similarly, deodorizing products of the invention that are themselves sanitized are a beneficial feature of the invention.

III. Microencapsulated Scented Oils

In some embodiments, the scented oils used in conjunction with the invention are applied to the solid substrate (for example, a paper) as encapsulated oils (such as microencapsulated oils) or oil-containing microparticles with a solid outer protective shell. Microencapsulation or generation of oil-containing particles brings a variety of benefits to the product, for example, providing enhanced oxidative stability, thermostability and extended shelf-life of the scented oils. In addition, microencapsulation or microparticle formation is also beneficial in controlling the volatility and premature release properties of the scented oils. Other benefits from the use of microencapsulation or microparticles of scented oils for use with the invention include increased stability of the scent-producing materials without the need for moisture-resistant and light-protective packaging.

Most generally, microencapsulation is a process of building a functional barrier between the core material (e.g., the scented oil) and the outside environment or material onto which the microencapsulation particle is adsorbed (e.g., onto a solid substrate such as a paper). Microencapsulation of the core material protects the inner core material from undesirable chemical reactions and premature physical release into the environment, and maintains, preserves or extends the functional and/or physicochemical properties of core materials. Any suitable microencapsulation materials and methodologies can be used with the present invention, as readily known to one of skill in the art. Similarly, methods for microparticle formation having solid or semi-solid exterior shells or homogenous dispersion of an oil in a solid particle are also known in the art, and find use with the invention. As used herein and in the art, the term "encapsulation" can refer to processes that use only liquid phases, or alternatively, can describe processes that employ solid or semi-solid materials to encapsulate a desired oil.

Microencapsulation can be achieved by employing any of a variety of different methods known in the art, including but not limited to emulsification and spray-drying.

In some embodiments, emulsification is used to generate suitable encapsulated particles containing scented oils finding use with the invention. Generally, the emulsion consists of at least two immiscible liquids, usually oil and water, with one of the liquids being dispersed as small spherical droplets in the other. There are several commonly used emulsion systems for producing encapsulated products, including (i) systems that consist of oil droplets dispersed in an aqueous phase: an oil-in-water (O/W) emulsion; (ii) systems that consist of water droplets dispersed in an oil phase, called a water-in-oil (W/O) emulsion; (iii) multiple emulsions, such as oil-in-water-in-oil (O/W/O) emulsions; and (iv) multiple emulsions consisting of water-in-oil-in-water (W/O/W) emulsions. To stabilize the formulations, emulsifiers or texture modifiers such as gelatin, alginate, pectin or starches can be optionally included.

The emulsions are generally prepared by homogenizing the oil (e.g., a scented oil), water, and emulsifier together using any suitable homogenizer device, as known in the art. The homogenized slurry may then be applied to a solid substrate, for example, a disintegratable paper, by spray-drying, wherein the slurry is dried with heat and air and atomized onto the solid substrate. The microcapsules produced by this technique measure between 1 and 100 microns and can be applied to the solid substrate, e.g., the disintegratable paper, on either one side or both sides of the paper.

Other suitable methodologies for applying microcapsules to the substrate include, but are not limited to, freeze-drying, complex coacervation and extrusion, as known in the art.

Protocols and materials for generating microencapsulated oils are known in the art, and are available from a variety of sources. See, for example, Bakry et al., "Microencapsulation of Oils: A Comprehensive Review of Benefits, Techniques, and Applications," Comprehensive Reviews in Food Science and Food Safety, published on-line November 2015, DOI: 10.1111/1541-4337.12179; and Fairhurst and Loxley, "Micro- and Nanoencapsulation of Water- and Oil-soluble Actives for Cosmetic and Pharmaceutical Applications," Chapter 17, published by Particle Sciences, Inc. (Bethlehem, Pa.); herein incorporated by reference in their entirety.

IV. Packaging

The methods and materials for packaging of the personal deodorizer sheets can vary, and is not particularly limited. In some embodiments, the personal deodorizer sheets are individually packaged in a manner where one personal deodorizer sheet is sealed in a suitable packaging or wrapping.

In other embodiments, the individually packaged deodorizing sheets can be repacked into multiple unit lots of any desired number for convenient retail sale. For example, 10 individually packaged deodorizing sheets can be boxed for sale as a single unit, or alternatively, any other number. Similarly, individually packaged deodorizing sheets of varying sizes or varying scent concentrations can be repacked into a single unit for sale.

The packaging can serve various beneficial functions, including (i) preventing moisture from reaching the deodorizer sheet and prematurely disintegrating the sheet, as might occur in humid environments, (ii) preventing the scent that is infused into the deodorizing sheet from prematurely escaping and scenting the local environment, and (iii) excluding damaging light wavelengths from the interior of the packet, thereby preventing photo-degradation of either the disintegratable paper and/or the scented oils.

The deodorizing sheet packaging can be labeled or decorated with any desired markings, designs, colors, or the like. Alternatively, the packaging can be plain, unadorned or unlabelled so that the packaged deodorizing sheets can be carried discreetly without revealing their contents. In some embodiments, the packaging containing the deodorizing sheets are small and flat so that they can be conveniently carried, for example, in a purse, wallet, handbag, pocket or the such.

It is not intended that the invention be limited to any particular type of packaging materials. In some embodiments, the personal deodorizer sheet is an individually packaged product that uses packaging materials that have some or all of the following characteristics:

(I) the packaging material is opaque (in part or whole); packaging that allows at least partial viewing of the contents can be appealing to consumers to view the contents and/or the attractive design of the product;

(II) the packaging material is fully impervious (fully opaque) to the transmission of wavelengths of light that can degrade the product (degrade either the paper substrate or the scented oil that is adsorbed onto the substrate;

(III) the packaging material is substantially impervious to liquid water and/or moisture in the air that can prematurely disintegrate the paper substrate or the scented oil; substantially impervious indicates that insignificant diffusion of water molecules may occur, but are in total of such small quantity and low rate as to have no consequence;

(IV) the packaging material is substantially impervious to the diffusion of molecules that carry scent, thereby preventing the scent from prematurely escaping the packaged product prior to opening and deployment; substantially impervious indicates that insignificant diffusion of scent molecules may occur, but are in total of such small quantity and low rate that there is no detectable scent emanating or leaching from an unopened packaged product.

In one embodiment, the deodorizing sheets are packaged using a laminated material, for example, a laminated material comprising a foil layer (an aluminum foil layer) and/or a polyethylene layer. The packaging materials can be multilayered polyethylene, foil or foil laminate, or any suitable paper product laminate, as known to one of skill in the art. Packaging material can optionally be recyclable packaging materials. In some embodiments, the deodorizing sheet as well as the packaging used for the product are 100% biodegradable.

In some embodiments, the deodorizing products of the invention are individually packaged in water-tight and air-tight packaging. When the products of the invention are individually packaged, the packaging can be sealed by any suitable method as widely known in the industry, for example, sealed by an adhesive, or sealed by a heat-sealing mechanism.

The individually packaged deodorizing sheets can be bundled into any desired size multiple package for convenient retail sale. Multiple units of individually packaged deodorizing sheets can be in any advantageous arrangement, for example, can be stacked in a box that has the ability to function as a dispenser, or can be on a roll of connected individually packaged deodorizing sheets, where the endmost packaged deodorizing sheet is torn from the roll along a pre-scored perforation. In some embodiments, individually packaged deodorizing sheets of various sizes or scent strengths can be incorporated into a single unit for retail sale, thereby giving the user an option to select a deodorizing sheet that will be more or less scented to a degree appropriate for the intended deodorizing task.

In one embodiment, the product is packaged in a foil-containing laminated wrapping material produced by ROASTAR DIGITAL POUCHES (Wausau, Wis.). The product is termed a matte laminate pouch. This particular product from ROASTAR DIGITAL POUCHES is a bright white material with a smooth satin finish suitable for printing and art/design application. The packet material is composed of layers, which are, in order of proximity to the product (innermost first):

1) 2 mil (0.002 inch) LLDPE (linear low-density polyethylene) Coextruded Peel
2) Polyethylene
3) Aluminum foil barrier
4) Polyethylene
5) Printed polyester
6) Print protective matte PET (polyethylene terephthalate) over laminate This particular packaging material, by way of non-limiting example, meets requirements for ink migration and packaging described in Title 21 Code of Federal Regulations §178.3530 from the Food and Drug Administration, Department of Health and Human Services. This example of packaging materials is also in compliance with standards set forth by the Coalition of Northeastern Governors (CONEG) for reducing the amounts of four heavy metals (mercury, lead, cadmium and hexavalent chromium) in packaging and packaging components.

Optionally, the packaging used with the deodorizing sheets can be of any type that facilitates opening the sealed package, ideally without the use of any mechanical aid such as scissors. The mechanism for opening a packaged product can be, for example but not limited to, a ZIPLOC®-style zipper sealing mechanism, tearing the packaging open or peeling apart two faces of the packaging (analogous to the packaging used in BAND-AID® brand adhesive bandages). To facilitate opening, the packaging can be prescored or perforated in any desired manner to facilitate tearing, for example, can contain a tear-strip along one edge of the product, be perforated at a corner, perforated along an edge or in some other section of the package that facilitates tearing open the packaging, nicked or contains a small pre-cut tear on the edge of the packet. In some embodiments, the packaging contains one or more pre-cut notches located approximately ⅜ of one inch from a corner of an equiangular quadrilateral, for example, when the packaging is square shaped or rectangular shaped.

Materials and methods suitable for packaging are well know to one of skill in the art, and it is not intended that the invention be limited in any regard with respect to a particular style of packaging or materials that are used to form the packaging.

Alternatively, or additionally, the individually packaged deodorizing sheets can be in the form of a contiguous roll of packaged deodorizing sheets, optionally where a single package can be torn away from the roll of packaged sheets along a pre-scored perforation, analogous to the dispensing of squares of toilet paper from a toilet paper roll.

Alternatively still, the deodorizing sheets need not be individually packaged, and can be processed for retail sale in packages containing a plurality of loose deodorizing sheets.

During the manufacturing process, the scented oil or scented oil blends are applied to the solid paper substrate at any convenient step. The scented oils can be applied to the solid substrate sheet before the sheet comes into contact with any of the packaging materials or packaging layers. Alternatively, the solid substrate sheet can first be placed on or in association with one layer of the packaging material, after which time, the scented oil is applied to the substrate, followed by application of the second layer of the packing and sealing the packaging material.

V. Uses

In some embodiments, the personal deodorizing sheets described herein are used to mask the user's toileting activities, and furthermore, does so in a manner that will not create an overpowering scent that calls attention to its deployment. In some embodiments, the scent that is emitted by the wetted (e.g., disintegrated) deodorizing sheets is sufficiently strong to conceal the toileting activity but remains understated and does not call attention to itself.

In other embodiments, the personal deodorizing sheets of the invention find utility in addition to masking toileting odors. The personal deodorizing sheets also find use without placing the product into water. The products of the invention can be used in their dry form to release a subtle scent from the infused solid substrate, for example, from the scented oil infused into a disintegratable paper. This scent can be triggered simply by opening the packaging of a single deodorizing sheet, for example, at one corner of the packaging, along one entire edge of the packaging, or by completely removing the scented sheet from the packaging.

Examples of other uses for the scented deodorizing sheets as personal air fresheners includes, but is not limited to, the following:

inside shoes or near shoes, especially offending malodorous shoes;
in drawers or closets as a sachet;
in automobiles, e.g., in lieu of hanging sachets or other artificial scents;
opened while using public transportation, such as busses, subways, trains, planes, ships, etc., where nearby odors may be unsavory;
in rooms (other than a toileting room) to ameliorate smoking, cooking, pet and other odors;
near litter boxes to mask pet odors;
in home health care facilities, e.g., in bedrooms and/or bathrooms;
in any space that is musty, smoky, or otherwise malodorous;
inside or near diaper pails or diaper changing stations;
in sinks or garbage disposals to reduce or mask odors from garbage disposal traps and drain traps.

The strength of the scent in the infused solid substrate can be modulated, and further, can be tailored to a particular intended use. For example, a more strongly scented sheet can be produced by applying a greater quantity of a scented oil to the solid substrate. Alternately, the deodorizing sheet can be produced in various sizes, thereby carrying more or less of the scented oil. Alternatively still, a stronger masking scent can be generated simply by opening and deploying more than one deodorizing sheet.

VI. Bulk Dispensers

In some embodiments, the deodorizing sheets are used in a commercial, industrial or public settings. In those instances, it is advantageous to provide a durable and refillable dispenser for distributing the deodorizing sheets, and furthermore, where the sheets are used in quantities greater than would typically be used in a residential setting. Durable bulk dispensers for dispensing deodorizing sheets are an aspect of the invention, and are within the purview of the invention. Such dispensers will employ novel dispensing mechanisms, as well as use specially manufactured deodorizing sheets in a manner that facilitates deployment from a bulk dispenser. Although the embodiments that follow describe bulk dispensers intended for high-traffic public spaces, smaller versions of these dispensers more suitable for home use are easily envisioned and constructed from these same designs.

The housings for the bulk dispensers can be any suitable material, preferably materials that are durable, washable, and have a finish that can withstand periodic sanitizing if necessary. Preferred materials include plastics or metals such as stainless steel. In some embodiments, the bulk dispensers are secured to a wall near the toilet, or are installed inside a toilet stall.

Any of the bulk dispensers describe herein can be operated by a mechanical mechanism, where the user presses a lever, turns a wheel or some other physical action results in dispensing of a scented paper product or a sealed individually packaged product. Alternatively, the bulk dispensers of the invention can be electronic, where by pushing a button or activation of a motion sensor, the electronic system which incorporates a motor will dispense a deodorizing paper or a sealed individually packaged product to the user.

Various designs for bulk dispensers are contemplated, as follows.

A) Bulk Dispensers Using a Sandwich of Two Layers of Product Packaging

In a first design, the deodorizing sheets are manufactured as a roll of deodorizing sheets, where the roll of product is housed within the bulk dispenser, and unwrapped product is dispensed from the device ready to be deployed into a toilet. The roll of deodorizing product for use in the device is manufactured using two layers of packaging for the product, namely, a top layer and a bottom layer. See FIGS. 5, 6, 7 and 9.

Figure 5:
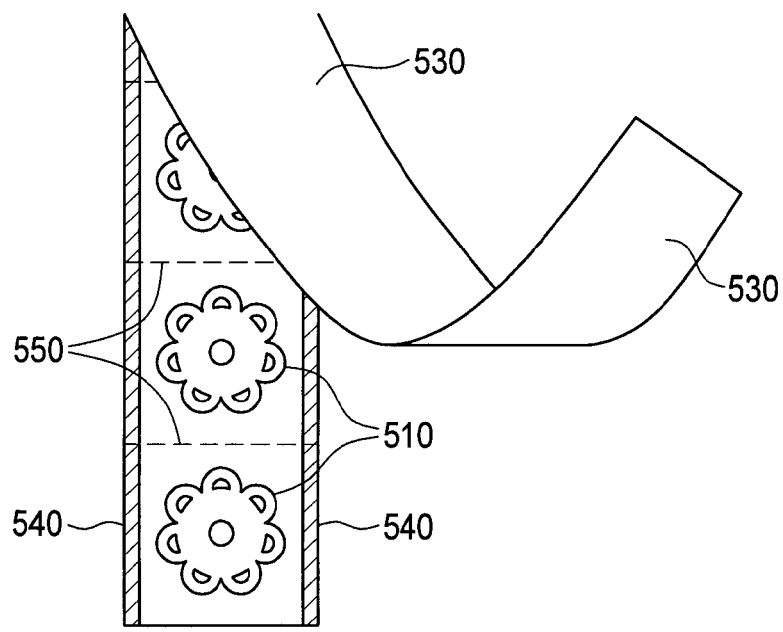
FIG. 5 provides an illustration depicting the manufacture of the deodorizing products of the invention in the form of a roll of products for use in bulk product dispensers.

FIG. 5 shows one embodiment for production of rolled deodorizing product for use in the bulk dispensers. The deodorizing product can be manufactured as strips of product. In this figure, the product is a scent-infused decorative paper disk 510. There is a bottom protective packaging layer 520, on which the scented disks 510 are placed. A top layer of packaging 530 is placed over the bottom layer 520 and paper disks 510. The two packaging layers are pressed together and the resulting sandwich is spooled onto a roll. Optionally, the roll of product can be manufactured by applying narrow rows of adhesive 540 to secure the top and bottom layers of packaging. Optionally, the adhesive can also be applied in narrow rows that are perpendicular to the rows of adhesive 540, for example, where adhesive is applied along the areas of the dashed lines 550, thereby forming a sealed package enclosing one scented deodorizing product 510.

The two layers of suitable packaging material 520 and 530 utilize any suitable material, for example, polyethylene, or a polyethylene-aluminum foil laminate, as known in the art. The bottom layer 520 and top layer 530 need not be made from the same material. Similarly, adhesive material 540, and any adhesive material applied to the regions 550 can be any type of adhesive material, for example, a heat-activated adhesive, as known in the art.

The paper disks 510 that are in the sandwich package can optionally be infused with the scented oil before they are incorporated into the sandwiching packaged. Alternatively, the paper disks can be infused after they are aligned on the bottom strip of packaging 520, but before application of the top layer of packaging 530.

FIG. 5 also depicts a more general strategy for production of individually packaged scented paper product that need not be used in a bulk dispenser. In this embodiment, a further strip of adhesive may be applied approximately at the dashed horizontal lines 550. In addition, the strip can be perforated at the dashed lines 550 so that individually wrapped product can be easily removed from the strip by tearing along the pre-scored perforated lines 550, analogous to tearing toilet paper squares from a toilet paper roll.

Figure 7:
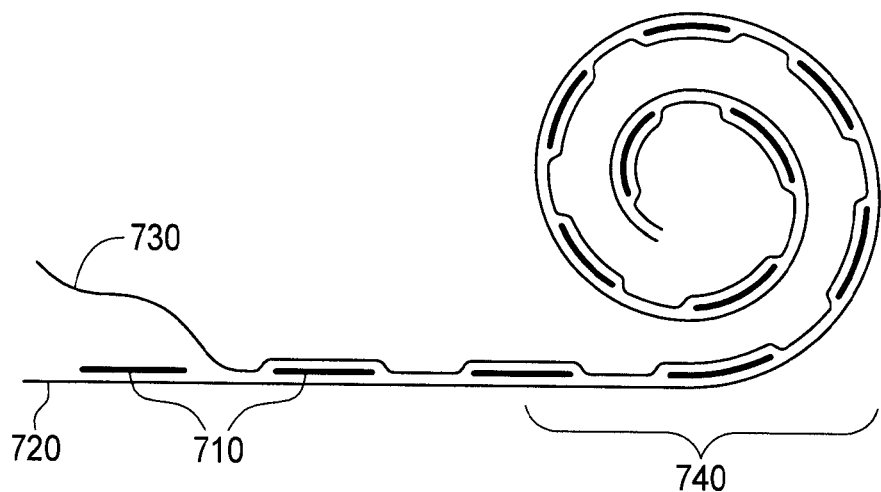
FIG. 7 provides an illustration depicting the general arrangement and manufacture of rolls of the deodorizing products of the invention for use in bulk product dispensers, where the product is sandwiched by two layers of protective wrapping.

FIG. 7 shows the general configuration of the rolled deodorizing product, consistent with the description of FIG. 5. In FIG. 7, the scented paper disks 710 are first applied to a bottom layer of packaging 720. The disks are then covered with a top layer of packaging 730. This sandwich is then wound into a roll 740 for efficient use of space where many scented disks are wound into a single compact roll 740 of products. The coiling of the roll of products 740 is much tighter than indicated in the illustration of FIG. 7.

Figure 6:
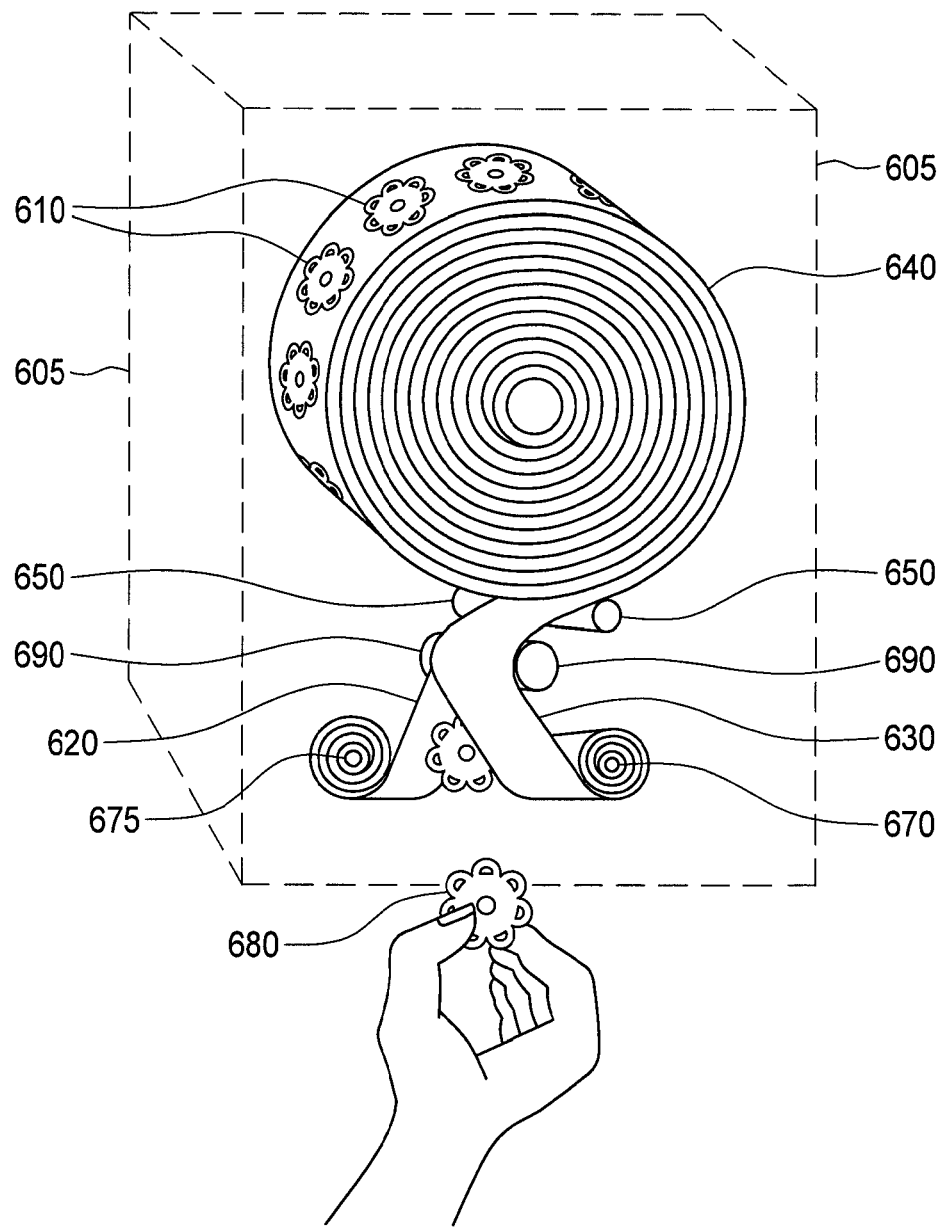
FIG. 6 provides an illustration depicting a device for the bulk dispensing of the deodorizing product of the invention.

One embodiment for a bulk dispenser is illustrated in FIG. 6. The bulk dispenser housing is shown in dashed line 605. Rolls 640 of deodorizing paper disk products 610 (consistent and according to FIGS. 5 and 7) are loaded into the device of FIG. 6. Each paper disk 610 on the roll of product 640 is sandwiched by a lower packaging layer 620 and an upper packaging layer 630. The strips of product are pulled from the roll 640 by a dispensing roller 650 and fed through separation rollers 690 that peel away the packaging material (e.g., polyethylene) for a predetermined unit length. At this point, the top packaging layer 630 is separated from the bottom layer of packaging 620. The separated and spent top layer of packaging 670 is spooled onto an uptake cog 660. Similarly, the separated and spent bottom layer of packaging 675 is spooled onto an uptake cog 665. Alternatively, a respool mechanism can be incorporated into the separation rollers in order to take up the spent wrappings. The dispensing roller and/or uptake cogs can be spring-loaded to accommodate the spent wrapping strips until the roll is used up.

The outermost scented paper disk 680 is released from the roll and held within the dispenser by a gripping mechanism that easily releases when the user grips and pulls the edge of the scented paper. The deodorizing paper disk emerges from the bulk dispenser already removed from the packaging. The paper disk can be released from the device by gentle pulling, or falls into a catch tray (not shown). Upon release, the disk is ready to be placed into the water of the toilet bowl. The remaining scented papers on the roll remain sealed within the wrapping sandwich until unsealed and released by the next user.

Figure 9:
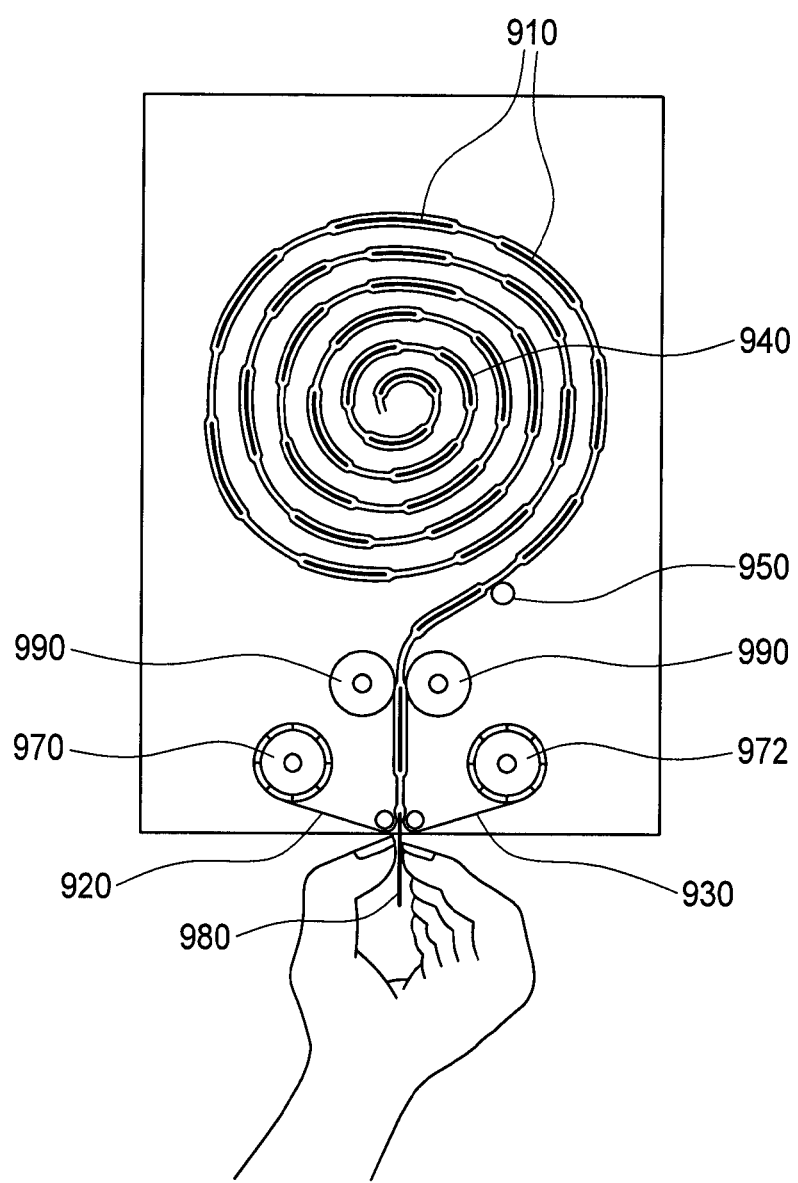
FIG. 9 provides a cross section schematic of a device for the bulk dispensing of the deodorizing product of the invention.

A lateral cross section view of a similar bulk dispensing device is provided in FIG. 9. The deodorizing paper disks 910 are sandwiched between two layers of a suitable packaging material to form strips. The packaging material can be any suitable material, for example, polyethylene, or a polyethylene-aluminum foil laminate. Alternatively, the deodorizing sheets can be sandwiched between layers of a foil-containing laminated wrapping material, for example, using materials that produce the matte laminate pouch manufactured by ROASTAR DIGITAL POUCHES (Wausau, Wis.), as described above.

The strips of deodorizing product are pulled from the roll 940 by a guide roller 950 and feed rollers 990. The strip is fed into separation rollers 970. At this point, the top packaging layer is separated from the bottom packaging layer. The separated top layer of packaging 920 is spooled onto an uptake cog 970. Similarly, the separated bottom layer of packaging 930 is spooled onto an uptake cog 972. The scented disk paper product 980 emerges from the bulk dispenser already unwrapped and ready to be placed into the water of the toilet bowl. The paper disk can be released from the device by gentle pulling, or falls into a catch tray (not shown).

When manufacturing the deodorizing sheets for spooling onto a roll (e.g., FIG. 7), the scented oil or scented oil blends are applied to the solid paper substrate at any convenient step. For example, the scented oils can be applied to the solid paper substrate 710 prior to the paper coming into contact with any of the packaging layers 720 or 730. Alternatively, the solid paper substrate 710 can first be placed on or in association with a first layer of the packaging material 720 (e.g., a bottom layer and/or an adhesive layer that holds the solid substrate in place), after which time, the scented oil is applied to the substrate, followed by application of the second layer of packing 730, e.g., a top layer, and then spooling onto a roll.

The materials and methods for the manufacture of scented papers for use in bulk dispensers more generally can be applied to the manufacture of individually packaged personal deodorizing scented papers. When two layers of packaging are used, the bottom layer of packaging or the top layer of packaging can be any suitable material, for example, a polyethylene, that may optionally contain an adhesive. The application of the bottom layer of packaging and the top layer of packaging forms a sandwich, where the scented solid substrate paper is in the middle of the sandwich. As shown in FIG. 5, cutting of this strip along pre-scored perforations 550 can generate individually packaged paper disks.

Figure 4:
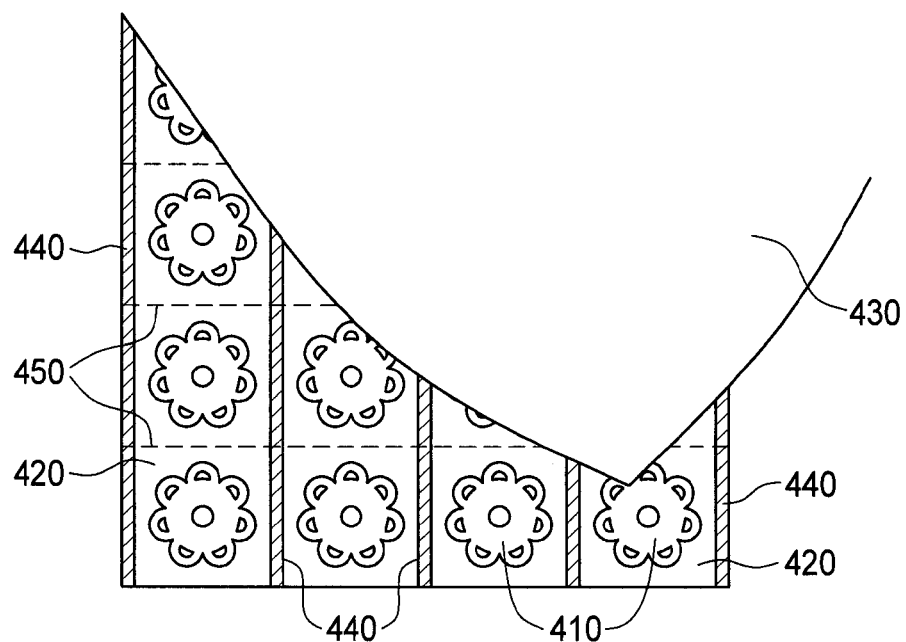
FIG. 4 provides an illustration depicting the manufacture of the deodorizing products of the invention in the form of sheets or pages of product.

Another embodiment of this process is shown in FIG. 4. Similar to FIG. 5, this sandwich configuration shown in FIG. 4 comprises a bottom layer of packaging 420, a top layer of packaging 430 and the sandwiched paper deodorizing disks 410. This method can also incorporate strips of glue or other adhesive in a vertical orientation 440 as well as a horizontal orientation. Advantageously, these products can be generated on large pages of packaging materials (FIG. 4) that can contain many individual products. These large sandwich pages are then cut into either individually packaged personal deodorizing papers, or can be cut into strips for use in bulk dispenser devices. Rows of perforations 450 can also be added to aid in release of individual packaged products.

Alternatively, when these pages of FIG. 4 are used to produce product for use in bulk dispensers, the pages of sandwich material are cut into strips, which are then sealed on the inner and outer edges; or cut into strips from a larger piece of the sandwiched material and sealed on inner and outer edges. The strips are rolled around a core, as tape is rolled around a core, where the first scented paper in the roll will form the center of the roll, and the outermost product is dispensed from the bulk device.

B) Bulk Dispensers Using One Layer of Packaging

Figure 8:
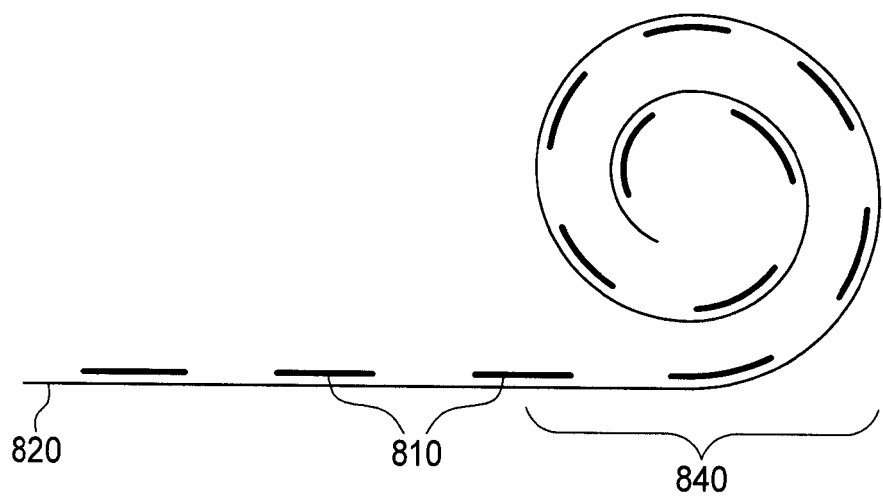
FIG. 8 provides an illustration depicting the general arrangement and manufacture of rolls of the deodorizing products of the invention for use in bulk product dispensers, where the product is packaged in a single layer of protective wrapping.

In a second dispenser design, similar to the first, the deodorizing sheets are also produced on long strips that are spooled onto a roll, but where there exists only a single layer of packaging separating the layers that are spooled onto the roll. See FIG. 8. In some embodiments, a variant design for the bulk dispenser is used, where the deodorizing papers 810 are manufactured as rolls 840, but where there is only a single layer of packaging material 820 separating the scented product when spooled into the roll 840.

In this design, only a single uptake cog is necessary to spool the spent sections of packaging that previously contacted the scented papers. For example, the uptake cog 660 in FIG. 6 is not required, and similarly, uptake cog 972 in FIG. 9 is also not necessary.

The use of this design has advantages, including a simpler unwrapping mechanism and easier production of the rolls of dispensed product. Because the coils of the rolled product can be made very tight, and both faces of the scented paper disks are still facing packaging material, that can minimize the release of fragrance from the scented oil on the paper disks.

C) Bulk Dispensers that Distribute Individually Packaged and Sealed Product

In a third contemplated design, the product is provided as individually packaged and sealed deodorizing sheets that are dispensed from the machine, and further, where the toilet user is required to open the packaging and deploy the product. The deodorizing product is not unwrapped prior to dispensing. In some embodiments, individually packaged and sealed personal deodorizer product is dispensed from a suitable bulk dispenser. In this aspect, the individually packaged and sealed products are loaded into a dispensing device. Actuation of the bulk dispenser device results in release of the individually packaged product to the user. The user then unwraps and deploys the scented paper product. This type of bulk dispenser has the advantage in that it can be tooled to accept a standard sized individually packaged deodorizer product, without the necessity to manufacture specially designed rolls of scented sheets.

Although this disclosure provides three examples (above) of bulk dispensers, one of skill in the art will recognize variant designs that are within the purview and spirit of the claimed invention. It is not intended that the invention be limited to any of the embodiments described herein; the examples described and shown herein only serve to illustrate but not limit the scope of the invention.

It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes combinations of two or more cells, or entire cultures of cells; reference to "a polynucleotide" includes, as a practical matter, many copies of that polynucleotide. Unless defined herein and below in the reminder of the specification, all technical and scientific terms used herein have the same meaning as commonly understood by one of ordinary skill in the art to which the invention pertains.

While the foregoing disclosure has been described in detail for purposes of clarity, it will be clear to one skilled in the art that trivial and inconsequential changes in form and detail can be made without departing from the scope of the invention. It is to be understood that the invention is not limited to any of the specifically recited methodologies or materials that are recited herein, where similar or equivalent methodologies or materials can be substituted and remain within the scope of the invention. It is understood that the description of various embodiments of the invention provided herein is for the purpose of illustrating the invention. It is not intended that the invention be limited solely to the embodiments described herein.

As used in this specification and the appended claims, singular forms such as "a", "an" and "the" include plural referents unless the content clearly dictates otherwise. For example, reference to "packaged deodorizing product" includes a plurality of packaged deodorizing products. All industry and technical terms used herein have the same meaning as commonly understood by one of ordinary skill in the art or industry to which the invention pertains, unless defined otherwise.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A composition comprising:
   (a) an aqueous-disintegratable paper solid substrate containing carboxymethyl cellulose, said aqueous-disintegratable paper solid substrate having a thickness between about 0.0025 inches and 0.005 inches, and
   (b) a non-aqueous scented liquid, where the non-aqueous scented liquid is infused into the aqueous-disintegratable paper solid substrate.

2. The composition of claim 1, wherein the aqueous-disintegratable paper solid substrate comprises at least one perforation.

3. The composition of claim 1, wherein the non-aqueous scented liquid is in sufficient quantity to abate odors when the composition is exposed to water.

4. The composition of claim 1, wherein the non-aqueous scented liquid comprises at least one scented oil.

5. The composition of claim 1, wherein the non-aqueous scented liquid comprises (i) at least one essential oil, (ii) at least one fragrance oil, (iii) at least one absolute oil, or (iv) any combination of scented liquids selected from (i), (ii) and (iii).

6. The composition of claim 1, wherein the non-aqueous scented liquid comprises a carrier oil.

7. A packaged deodorizing product comprising:
   (a) an aqueous-disintegratable paper solid substrate containing carboxymethyl cellulose, said aqueous-disintegratable paper solid substrate having a thickness between about 0.0025 inches and 0.005 inches, infused with a non-aqueous scented liquid, thus producing a scent-infused aqueous-disintegratable paper solid substrate, and
   (b) sealed packaging comprising the scent-infused aqueous-disintegratable paper solid substrate, wherein the sealed packaging is substantially impervious to water.

8. The packaged deodorizing product of claim 7, wherein the sealed packaging is substantially impervious to diffusion of scent-inducing molecules.

9. The packaged deodorizing product of claim 7, wherein the sealed packaging is opaque.

10. The packaged deodorizing product of claim 7, wherein the non-aqueous scented liquid comprises at least one scented oil.

11. The packaged deodorizing product of claim 7, wherein the non-aqueous scented liquid comprises (i) at least one essential oil, (ii) at least one fragrance oil, (iii) at least one absolute oil, or (iv) any combination of scented liquids selected from (i), (ii) and (iii).

12. The packaged deodorizing product of claim 7, wherein the non-aqueous scented liquid comprises a carrier oil.

\* \* \* \* \*